United States Patent
Hanusse

(10) Patent No.: US 9,649,051 B2
(45) Date of Patent: *May 16, 2017

(54) METHOD AND SYSTEM FOR ANALYZING A PATIENTS RESPIRATORY ACTIVITY AND CORRESPONDING USES

(75) Inventor: Patrick Hanusse, Pessac (FR)

(73) Assignee: CENTRE NATIONAL DE LA RECHERCHE SCIENTIFIQUE (C.N.R.S), Paris (FR)

( * ) Notice: Subject to any disclaimer, the term of this patent is extended or adjusted under 35 U.S.C. 154(b) by 1149 days.

This patent is subject to a terminal disclaimer.

(21) Appl. No.: 13/695,266

(22) PCT Filed: Apr. 28, 2011

(86) PCT No.: PCT/FR2011/050957
§ 371 (c)(1),
(2), (4) Date: Dec. 20, 2012

(87) PCT Pub. No.: WO2011/135257
PCT Pub. Date: Nov. 3, 2011

(65) Prior Publication Data
US 2013/0096452 A1    Apr. 18, 2013

(30) Foreign Application Priority Data

Apr. 30, 2010 (FR) .................................. 10 53357

(51) Int. Cl.
*A61B 5/08* (2006.01)
*A61B 5/087* (2006.01)
(Continued)

(52) U.S. Cl.
CPC ............... *A61B 5/087* (2013.01); *A61B 5/72* (2013.01); *A61B 5/7225* (2013.01);
(Continued)

(58) Field of Classification Search
CPC ..... A61B 5/087; A61B 5/7225; A61B 5/7278; A61B 5/72; A61B 5/7271; A61B 5/7275;
(Continued)

(56) References Cited

U.S. PATENT DOCUMENTS 5,020,540 A     6/1991  Chamoun
6,306,088 B1 * 10/2001  Krausman .......... A61B 5/02055
                                                    600/301
(Continued)

FOREIGN PATENT DOCUMENTS

FR           2955187 A1     7/2011

OTHER PUBLICATIONS

Centre De Recherche Paul Pascal (CRPP) Oct. 9, 2005 Presentation entitled "Presentation de l'equipe Structures et dynamiques non-lineaires." (XP007917496).

(Continued)

*Primary Examiner* — Patricia Mallari
*Assistant Examiner* — Karen Toth
(74) *Attorney, Agent, or Firm* — Knobbe, Martens, Olson & Bear, LLP

(57) ABSTRACT

A method for analyzing the respiratory activity of a patient includes steps for acquiring at least one respiratory activity signal including at least one elementary signal corresponding to a respiratory cycle, the general form of which may be expressed by $x(t)=x_0+x_1 \cos(\Phi(t))$, wherein $\Phi(t)$ is the phase of the elementary signal, and for analyzing the respiratory activity signal. The analysis includes steps for extracting, from the respiratory activity signal, the elementary signal, for determining an expression of a phase equation (Continued)

$$F(\Phi) = \frac{d\Phi}{dt}$$

of the elementary signal and for determining an expression of the phase Φ(t) of the elementary signal as a function of parameters measuring the anharmonicity of the elementary signal and its morphology, from p cos$_n$ and p sin$_n$ functions defined by:

$$p\cos_n(t, r) = \sum_{k=1}^{\infty} \cos(kt)\frac{r^k}{k^n} \text{ and } p\sin_n(t, r) = \sum_{k=1}^{\infty} \sin(kt)r\frac{r^k}{k^n}.$$

5 Claims, 1 Drawing Sheet

(51) Int. Cl.
    *A61B 5/00*           (2006.01)
    *A61M 16/00*        (2006.01)
    *A61M 16/06*        (2006.01)
    *G06F 17/14*         (2006.01)

(52) U.S. Cl.
    CPC .......... *A61B 5/7271* (2013.01); *A61B 5/7275* (2013.01); *A61B 5/7278* (2013.01); *A61M 16/00* (2013.01); *A61M 16/06* (2013.01); *G06F 17/141* (2013.01)

(58) Field of Classification Search
    CPC . G06F 17/14; A61M 2230/005; A61M 16/00; A61M 16/0069; A61M 16/06; A61M 2016/0036; A61M 2016/003
    See application file for complete search history.

(56) References Cited

U.S. PATENT DOCUMENTS

| | | | | |
|---|---|---|---|---|
| 8,694,566 B2* | 4/2014 | Hanusse | ............... | G06F 17/141 708/270 |
| 8,731,647 B2* | 5/2014 | Hanusse | ............. | A61B 5/0452 600/510 |
| 2001/0027792 A1* | 10/2001 | Berthon-Jones | ...... | A61M 16/00 128/204.23 |

OTHER PUBLICATIONS

Centre De Recherche Paul Pascal (CRPP) listing of presentation by Hanusse, P. on Oct. 8, 2008 "Phénomènes périodiques non-linéaires: Théorie de l'anharmonicité" (see p. 20). (XP007917497).
Hanusse, P. Mar. 10-12, 2010 "Théorie de l'anharmonicité des phénomènes périodiques non-linéaires" Résumé d'un exposé soumis pour la 13e rencontre du Non-Linéaire. (XP055012353).
Hanusse, P. 2011 "A novel approach to anharmonicity for a wealth of applications in nonlinear science technologies" *International Conference on Applications in Nonlinear Dynamics—ICAND2010* 1339: 303-308. (XP055012260).
Institut Henri Poincare 2010 Résumés des exposés de la 13e Rencontre du Non-Linéaire, located on the internet at: nonlineaire. univ-lillel.fr/SNL/media/2010/resumes/ResumesRNL2010sel.pdf, (see p. 24). (XP055012351).
Institut Henri Poincare 2010 Résumés des exposés de la 13e Rencontre du Non-Linéaire, located on the internet at: nonlineaire. univ-lillel.fr/SNL/media/2010/resumes/ResumesRNL2010sel.pdf, (see Table des matières). (XP055012352).
Kraskov, A. et al. 2004 "Extracting phases from aperiodic signals" located on the internet at: arxiv.org/pdf/cond-mat/0409382.pdf. (XP002627501).
Science Non-Lineaire 2010 "Index of /SNL/media/2010/resumes" located on the Serveur du site Internet de la 13e Rencontre du Non Lineaire, Mar. 10-12, 2010, Paris, France, located on the internet at: nonlineaire.univ-lille1.fr/SNL/media/2010/resumes. (XP055012387).
Science Non-Lineaire 2010 "Programme de la 13e Rencontre du Non-Lineaire" located on the Serveur du site Internet de la 13e Rencontre du Non Lineaire, Mar. 10-12, 2010, Paris, France, located on the internet at: nonlineaire.univ-lille1.fr/SNL/media/ 2010/programme/ProgrammeRNL2010.pdf. (XP055012355).

* cited by examiner

METHOD AND SYSTEM FOR ANALYZING A PATIENTS RESPIRATORY ACTIVITY AND CORRESPONDING USES

FIELD OF THE INVENTION

The present invention relates to a method and a system for analyzing the respiratory activity of a patient, the method comprising the steps for acquiring at least one respiratory activity signal comprising at least one elementary signal corresponding to a respiratory cycle, the general form of which may be expressed by $x(t)=x_0+x_1 \cos(\Phi(t))$, wherein $\Phi(t)$ is the phase of said elementary signal, and for analyzing said respiratory activity signal.

It also relates to the applications of the latter to the control of a respiratory assistance device and a respiratory monitoring device.

It applies in particular to the detection of respiratory disorders or to the control of artificial ventilation devices.

BACKGROUND OF THE INVENTION

A respiratory activity signal is a signal measuring the variation of a quantity related to the respiratory activity of the patient, such as the air flow rate and pressure or the oxygen and carbon dioxide concentration at the entry of his/her respiratory tracts or the oxygen concentration in the blood. These quantities may be measured with non-invasive measuring apparatuses, for example a flow rate or pressure sensor integrated to a mask placed in front of the mouth of the patient or an oxymeter, or with internal sensors, for example pressure sensors, placed in the respiratory circuit of the patient. Such signals may also be inferred from electrocardiogram signals.

Respiratory activity consists of a succession of respiratory cycles, comprising an inhalation phase and exhalation phase, at a frequency called a respiratory frequency. Therefore, the respiratory activity signals are quasi-periodic signals, comprising a succession of elementary signals, each of these elementary signals being characteristic of a respiratory cycle.

The analysis of these signals allows detection of respiratory disorders or abnormalities such as sleep apnea or asthma. However, this analysis is generally limited to the determination of the respiratory frequency and of its variability, and of the amplitude of these signals, and no analysis of the waveform of these signals is carried out.

Now, the waveform of respiratory activity signals is characteristic of this respiratory activity and their analysis may allow efficient detection of possible respiratory abnormalities.

Many methods for analyzing and characterizing a periodic signal are known. In particular, frequency analysis of a signal allows a description of this signal in Fourier space. Fourier decomposition actually consists in breaking down a periodic signal of frequency f into an infinite sum of sinusoidal functions with frequencies which are multiples of f, weighted with Fourier coefficients. These Fourier coefficients, which form a coding of the analyzed signal, are characteristic parameters of this signal. In practice, the number of retained Fourier coefficients is limited and only the first terms of the Fourier decomposition are kept. These terms however have to be in sufficient number in order to characterize the signal efficiently.

Now, respiratory activity signals are anharmonic signals, i.e. non-linear signals, and the Fourier decomposition of such signals requires that a large number of coefficients be retained, coefficients to which it is difficult to give a physical meaning. Fourier decomposition is therefore unsuitable for analyzing these signals.

SUMMARY OF THE INVENTION

Therefore the object of the invention is to allow the analysis of waveforms of respiratory activity signals by means of a small number of parameters bearing a physical meaning and forming a simple and explicit signature of the shape of these signals.

For this purpose, the object of the invention is an analysis method of the aforementioned type, characterized in that the analysis of the respiratory activity signal comprises the following steps:

extracting from said respiratory activity signal, said elementary signal;

determining an expression of a phase equation $$F(\Phi) = \frac{d\Phi}{dt}$$

of said elementary signal; and determining an expression of the phase $\Phi(t)$ of said elementary signal as a function of parameters ($r$, $r_k$, $\Phi_0$, $p_k$) measuring the anharmonicity of said elementary signal and its morphology, from $p \cos_n$ and $p \sin_n$ functions defined by:

$$p\cos_n(t, r) = \sum_{k=1}^{\infty} \cos(kt)\frac{r^k}{k^n} \text{ and } p\sin_n(t, r) = \sum_{k=1}^{\infty} \sin(kt)r\frac{r^k}{k^n}.$$

The method according to the invention also includes the following characteristics taken separately or as a combination:

the phase equation is expressed as:

$$\frac{d\Phi}{dt} = \frac{1+r^2+2r\cos(\Phi)}{1-r^2},$$

wherein r varying in [0,1] is a parameter measuring the anharmonicity of said elementary signal;

the elementary signal is expressed by means of two parameters r and $\Phi_0$, as:

$x(t)=x_0+a_1 h \sin(t,r)+b_1 h \cos(t,r)$ wherein $a_1=x_1 \cos(\Phi_0)$ and $b_1=-x_1 \sin(\Phi_0)$, the h sin and h cos functions being defined by:

$$h\cos(t, r) = \frac{(1+r^2)\cos(t)-2r}{1+r^2-2r\cos(t)} \text{ and }$$

$$h\sin(t, r) = \frac{(1-r^2)\sin(t)}{1+r^2-2r\cos(t)};$$

the phase equation is expressed as:

$$F(\Phi) = \frac{P(\Phi)}{Q(\Phi)},$$

wherein P(Φ) and Q(Φ) are trigonometric polynomials;
the expression of the phase Φ(t) is determined as:

$$t(\Phi) = \Phi + \sum_{k=1}^{n} a_k p\sin_1(\Phi - p_k, r_k) - b_k p\cos_1(\Phi - p_k, r_k)$$

wherein the p sin$_1$ and p cos$_1$ functions are defined by:

$$p\cos_1(t, r) = \sum_{k=1}^{\infty} \cos(kt)\frac{r^k}{k} \text{ and}$$

$$p\sin_1(t, r) = \sum_{k=1}^{\infty} \sin(kt)\frac{r^k}{k}.$$

The method according to the invention achieved in this way, allows analysis of respiratory activity signals and characterization of these signals by means of a small number of parameters, as compared with the methods for analyzing periodic signals according to the state of the art. Further, these parameters have a physical meaning and are characteristic of the waveforms of these signals.

According to another aspect, the object of the invention is also a system for analyzing the respiratory activity of a patient comprising means for acquiring a respiratory activity signal comprising at least one elementary signal corresponding to a respiratory cycle, the general form of which may be expressed by $x(t)=x_0+x_1 \cos(\Phi(t))$, wherein Φ(t) is the phase of said elementary signal, and means for analyzing said respiratory activity signal, characterized in that the means for analyzing said respiratory activity signal comprise:

means for extracting from said respiratory activity signal, said elementary signal;
means for determining an expression of a phase equation $$F(\Phi) = \frac{d\Phi}{dt}$$

of said elementary signals; and means for determining an expression of the phase Φ(t) of said elementary signal as a function of parameters (r, $r_k$, $\Phi_0$, $p_k$) measuring the anharmonicity of said elementary signal and its morphology from the p cos$_n$ and p sin$_n$ functions defined by:

$$p\cos_n(t, r) = \sum_{k=1}^{\infty} \cos(kt)\frac{r^k}{k^n} \text{ and}$$

$$p\sin_n(t, r) = \sum_{k=1}^{\infty} \sin(kt)\frac{r^k}{k^n}.$$

The system according to the invention also includes the following characteristics, taken separately or as a combination:

the system includes means for expressing the phase equation as:

$$\frac{d\Phi}{dt} = \frac{1 + r^2 + 2r\cos(\Phi)}{1 - r^2},$$

wherein r, varying in [0,1], is a parameter measuring the anharmonicity of said elementary signal;

the system includes means for expressing said elementary signal by means of two parameters r and $\Phi_0$, as:

$$x(t)=x_0+a_1 h \sin(t,r)+b_1 h \cos(t,r)$$

wherein $a_1=x_1 \cos(\Phi_0)$ and $b_1=-x_1 \sin(\Phi_0)$, the h sin and h cos functions being defined by:

$$h\cos(t, r) = \frac{(1 + r^2)\cos(t) - 2r}{1 + r^2 - 2r\cos(t)} \text{ and}$$

$$h\sin(t, r) = \frac{(1 - r^2)\sin(t)}{1 + r^2 - 2r\cos(t)};$$

the system includes means for expressing the phase equation as:

$$F(\Phi) = \frac{P(\Phi)}{Q(\Phi)},$$

wherein P(Φ) and Q(Φ) are trigonometric polynomials;
the system includes means for expressing the phase Φ(t) as:

$$t(\Phi) = \Phi + \sum_{k=1}^{n} a_k p\sin_1(\Phi - p_k, r_k) - b_k p\cos_1(\Phi - p_k, r_k)$$

wherein the p sin$_1$ and p cos$_1$ functions are defined by:

$$p\cos_1(t, r) = \sum_{k=1}^{\infty} \cos(kt)\frac{r^k}{k} \text{ and } p\sin_1(t, r) = \sum_{k=1}^{\infty} \sin(kt)r\frac{r^k}{k}.$$

According to other aspects, the object of the invention is also a respiratory assistance device and a system for analyzing respiratory activity comprising a system for analyzing respiratory activity according to the invention.

BRIEF DESCRIPTION OF THE DRAWINGS

The invention will be better understood with reference to an exemplary embodiment of the invention which will now be described with reference to the appended drawings wherein.

DETAILED DESCRIPTION OF CERTAIN EMBODIMENTS

Figure 1:
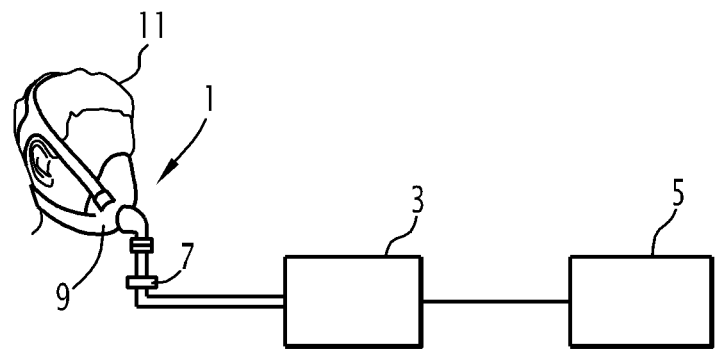
FIG. 1 schematically illustrates an analysis system according to an embodiment of the invention.

A system for acquiring and analyzing respiratory activity signals is illustrated in FIG. 1.

This system comprises means 1 for acquiring a respiratory activity signal, an acquisition box 3, connected to the acquisition means 1 and means 5 for analyzing a respiratory activity signal, for example a processor, connected to the acquisition box 3.

The acquisition means 1 are capable of collecting a respiratory activity signal. As an example, these means 1 comprise a pneumotachograph 7, placed at the outlet of a respiratory mask 9 covering the nose and the mouth of a patient 11. The pneumotachograph 7 is capable of continuously measuring the flow rate of inhaled and exhaled air by the patient 11 and of transmitting to the acquisition box 3, an analog electric signal characteristic of this flow rate.

The acquisition box 3 comprises an analog/digital converter, capable of converting an analog signal to a digital signal, subsequently called a respiratory activity signal, by sampling and quantifying the analog signal.

The processor 5 is capable of analyzing a digital respiratory signal so as to extract therefrom characteristic parameters of the shape of this signal.

Figure 2:
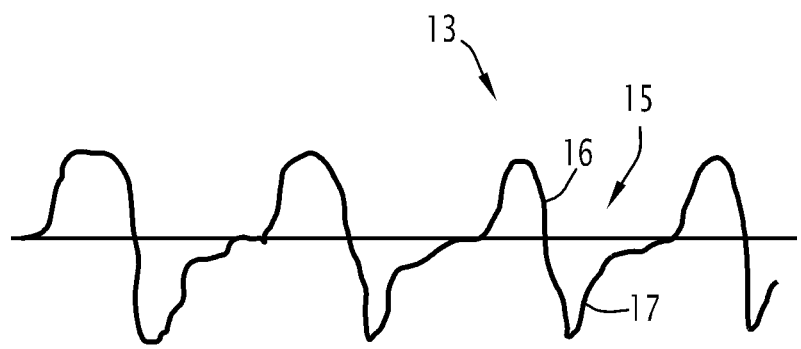
FIG. 2 illustrates a respiratory activity signal.

A plot illustrating the shape of a respiratory activity signal 13 as measured by the pneumotachograph 7 is illustrated in FIG. 2. In this plot, time is illustrated in abscissae and the air flow rate, from the outside towards the respiratory apparatus of the patient 11, in ordinates. Four elementary signals 15 may be recognized on this plot, each corresponding to a respiratory cycle, comprising an inhalation phase 16, during which the flow rate is positive and an exhalation phase 17, during which the flow rate is negative.

Figure 3:
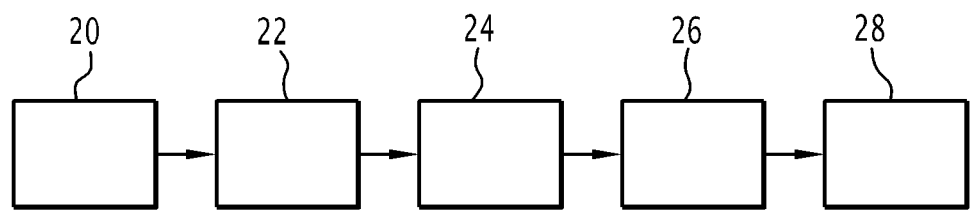
FIG. 3 is a block diagram illustrating the method according to an embodiment of the invention.

FIG. 3 is a block diagram illustrating the acquisition and analysis of a respiratory activity signal by means of the system described with reference to FIG. 1, according to an embodiment of the invention.

In a first acquisition step 20, the inhaled and exhaled air flow rate by the patient 11 is measured with the pneumotachograph 7, which continuously transmits to the acquisition casing 3 an analog electric signal, the instantaneous amplitude of which is proportional to the measured flow rate.

This analog signal is digitized in a step 22 by the analog/digital converter of the acquisition box 3, by sampling and quantification, and the thereby digitized signal or respiratory activity signal is transmitted to the processor 5.

This respiratory activity signal 13 consists of a succession of elementary signals 15, each corresponding to a respiratory cycle. However it is not strictly periodic, notably because of the variability of the respiratory frequency and of the flow rate of inhaled and exhaled air during each of the cycles. Therefore the instantaneous respiratory period is defined as the time interval between the beginning of a respiratory cycle, i.e. the onset of its inhalation phase, and the beginning of the preceding respiratory cycle.

In one step 24, the processor breaks down the respiratory activity signal 13 into elementary signals 15. This decomposition may for example be carried out by detecting the instant at which the signal passes from a negative value to a positive value, which corresponds to a transition between the exhalation phase of a cycle and the inhalation phase of the next cycle. Thus, during step 24, the processor determines the instantaneous frequency of the patient and its variability.

Next, the processor 5 analyzes in a step 26 each of the elementary signals 15 from this decomposition.

Each elementary signal x(t) is an anharmonic signal, which may be described in the following form:

$$x(t) = x_0 + x_1 \cos(\Phi(t)) \tag{1}$$

wherein all the time dependency is contained in the phase function $\Phi$.

This elementary signal x(t) is considered as a period signal of period T, T being equal to the reciprocal of the instantaneous respiratory frequency.

Now, in an anharmonic signal, the main contribution to anharmonicity comes from the breaking of the symmetry of the phase dynamics. Thus, all the relevant dynamic information is expressed by the phase dynamics. During the analysis of the signal x(t), this phase $\Phi(t)$ should therefore by studied, and in particular the phase dynamics expressed by the function F, the derivative of the function $\Phi$ with respect to time t:

$$F(\Phi) = \frac{d\Phi}{dt} \tag{2}$$

Thus, the morphology of the signal x(t) is completely determined by the knowledge of F.

The analysis step 26 of the method according to the invention therefore consists of describing this function F by means of a very small number of parameters. By small number of parameters, is meant a reduced number of parameters relatively to the number of parameters required for breaking down the same function, by means of Fourier series, with an equivalent accuracy level.

This analysis step 26 thus comprises a first step consisting of expressing the phase $\Phi$, and in particular function F, the time derivative of $\Phi$.

In the simplest case and for a signal of period $2\pi$, the phase dynamics may be written as:

$$F(\Phi) = \frac{d\Phi}{dt} = \frac{1 + r^2 + 2r\cos(\Phi)}{1 - r^2} \tag{3}$$

called the phase equation.

The function F in this case has reflection symmetry with respect to the axis for $\Phi=0$. This expression of the phase dynamics only contains a single parameter r, which varies in the interval [0,1]. The limit r=0 corresponds to a harmonic signal, the limit r=1 to an infinitely anharmonic signal.

The signal x(t), which may be written as:

$$x(t) = x_0 + x_1 \cos(\Phi(t,r) - \Phi_0) \tag{4}$$

wherein $\Phi_0$ is a phase origin, is broken down and rewritten in a form involving the parameters r and $\Phi_0$:

$$x(t) = x_0 + a_1 h \sin(t,r) + b_1 h \cos(t,r) \tag{5}$$

with $a_1 = x_1 \cos(\Phi_0)$ and $b_1 = -x_1 \sin(\Phi_0)$, and wherein the following h cos and h sin functions are defined by:

$$h\cos(t, r) = \frac{(1 + r^2)\cos(t) - 2r}{1 + r^2 - 2r\cos(t)} \tag{6}$$

$$h\sin(t, r) = \frac{(1 - r^2)\sin(t)}{1 + r^2 - 2r\cos(t)} \tag{7}$$

Thus, the decomposition of the signal x(t) only involves two parameters r and $\Phi_0$.

r, called an anharmonicity parameter, measures the degree of anharmonicity of the signal, the limit r=0 corresponds to a harmonic signal, the limit r=1 to an infinitely anharmonic signal. Moreover, the parameter $\Phi_0$ which defines the composition of the signal in both h cos and h sin functions is a morphology parameter, which corresponds to the angle of reflection symmetry of the phase dynamics.

In the general case, i.e. for any periodic signal, the phase equation may be written as:

$$F(\Phi) = \frac{P_n(\Phi)}{Q_m(\Phi)} \quad (8)$$

wherein $P_n$ and $Q_m$ are trigonometric polynomials of respective degrees n and m. The general form of a trigonometric polynomial of degree n is:

$$P_n(\Phi) = a_0 + \sum_{k=1}^{n} a_k \cos(k\Phi) + b_k \sin(k\Phi) \quad (9)$$

The analysis of the signal x(t) then comprises the determination of an expression of $\Phi$ involving a small number of parameters, which allows determination of expression of the signal x(t) as a function of these parameters.

Advantageously, the phase equation (2) may be rewritten as:

$$\frac{1}{F(\Phi)} = \frac{dt}{d\Phi} = \frac{Q_m(\Phi)}{P_n(\Phi)} \quad (10)$$

Factorization of the polynomial $P_n(\Phi)$ allows transformation of $$\frac{1}{F(\Phi)}$$

into a sum or simple terms, which allows the phase equation to be rewritten as:

$$\frac{dt}{d\Phi} = a_0 + \sum_{k=1}^{n} \frac{a_k \cos(\Phi - p_k) + b_k \sin(\Phi + p_k)}{(1 + r_k^2 - 2r_k \cos(\Phi + p_k))} \quad (11)$$

Wherein the parameters $r_k$, comprised between 0 and 1, measure the anharmonicity of the signal x(t) and the parameters $p_k$ characterize its morphology.

The period T of the signal may be determined by integrating this equation with respect to $\Phi$, between 0 and $2\pi$:

$$T = \int_{\Phi=0}^{\Phi=2\pi} \frac{d\Phi}{F(\Phi)} = 2\pi \left( a_0 + \sum_k \frac{r_k a_k}{1 - r_k^2} \right) \quad (12)$$

From this result and from constraints according to which the period is equal to $2\pi$ and the signal is harmonic when the coefficients $r_k$ are all zero, the phase equation may be expressed as:

$$\frac{dt}{d\Phi} = 1 + \sum_{k=1}^{n} D_k(\Phi - p_k) \quad (13)$$

Where the function $D_k$ is defined by:

$$D_k : \Phi \to \frac{r_k(a_k \cos(\Phi) + b_k \sin(\Phi) - a_k)}{(1 + r_k^2 - 2r_k \cos(\Phi))} \quad (14)$$

And verifies:

$$\int_{\Phi=0}^{\Phi=2\pi} D_k(\Phi) d\Phi = 0 \quad (15)$$

The definition of the poly cos and poly sin functions, noted as $p\cos_n$ and $p\sin_n$, which are expressed by:

$$p\cos_n(t, r) = \sum_{k=1}^{\infty} \cos(kt) \frac{r^k}{k^n} \quad (16)$$

$$p\sin_n(t, r) = \sum_{k=1}^{\infty} \sin(kt) \frac{r^k}{k^n} \quad (17)$$

and have inter alia the following properties:

$$p\cos_0(t, r) = \frac{r(\cos(t) - r)}{1 + r^2 - 2r\cos(t)} \quad (18)$$

$$p\sin_0(t, r) = \frac{r \sin(t)}{1 + r^2 - 2r\cos(t)} \quad (19)$$

$$p\cos_1(t, r) = -\frac{1}{2} \ln(1 + r^2 - 2r\cos(t)) \quad (20)$$

$$p\sin_1(t, r) = \tan^{-1}\left(\frac{r \sin(t)}{1 - r\cos(t)}\right) \quad (21)$$

allows the phase equation to be rewritten as:

$$\frac{dt}{d\Phi} = 1 + \sum_{k=1}^{n} a_k p\cos_0(\Phi - p_k, r_k) + b_k p\sin_0(\Phi - p_k, r_k) \quad (22)$$

By solving this equation it is possible to access an analytical expression of $t(\Phi)$ which is expressed by:

$$t(\Phi) = \Phi + \sum_{k=1}^{n} a_k p\sin_1(\Phi - p_k, r_k) - b_k p\cos_1(\Phi - p_k, r_k) \quad (23)$$

The time t is therefore expressed as a function of the phase $\Phi$, and in a dual way, the phase $\Phi$ is expressed as a function of the time t, by means of clearly defined independent parameters, which measure anharmonicity (parameters r or $r_k$), and the morphology (parameters $\Phi_0$ or $p_k$).

Thus, during the analysis step 26, the processor 5 encodes each elementary signal x(t) by means of a small number of parameters. According to an embodiment, each elementary signal x(t) is described almost exactly by an amplitude, a harmonicity r and a morphology $\Phi_0$. According to another embodiment, each elementary signal x(t) is described in an even more accurate way by two pairs of parameters ($r_1$, $p_1$) and ($r_2$, $p_2$), completed with their respective weights.

Each of the elementary signals, therefore each respiratory cycle, is therefore characterized by a restricted number of parameters, bearing a physical meaning since they are representative of the non-linearity and morphology of this signal.

Next, in a step 28, the processor compares the values of the parameters determined for each elementary signal, i.e. the instantaneous respiratory frequency, the amplitude and the morphology and harmonicity parameters of the signal, with tabulated values of parameters recorded beforehand, so as to detect possible respiratory abnormalities.

The method according to the invention thus allows analysis of respiratory activity and extraction of a respiratory activity signal, of a restricted number of parameters, allowing a compact and relevant representation of the waveform of the signal, and specific detection of possible respiratory abnormalities.

The steps 20, 22, 24, 26 and 28 may be carried out gradually as the respiratory activity signal is acquired, so as to continuously monitor the respiratory activity of the patient.

According to another embodiment, the system and the method according to the invention may be applied in an artificial respirator.

An artificial respirator is a device aiming at compensating for respiratory failure of a patient, by blowing air towards the lungs of a patient via a mask, by means of a fan. In order that this ventilation be efficient, it is necessary to synchronize the inhalation efforts of the patient and the triggering of the fan, i.e. air is blown into the lungs by the fan only during the inhalation phase of the respiratory cycle of the patient.

By measuring the inhaled and exhaled air flow rate by the patient, it is possible to detect the beginning and the end of this inhalation phase, and thereby synchronize the operation of the fan on the respiratory cycle of the patient.

This detection is generally achieved by setting two flow rate or pressure thresholds, the fan being actuated as soon as the flow rate or the pressure of inhaled air by the patient exceeds a first threshold and stopped as soon as this flow rate or this pressure becomes lower than a second threshold.

This detection method may prove to be inefficient, notably because of the variability of the respiratory cycles, leading to inadequacy between the set flow rate thresholds and these respiratory cycles. This inadequacy may cause poor synchronization between the fan and the patient or even non-triggering of the fan.

Thus, according to an embodiment of the invention, the method for analyzing the respiratory activity according to the invention is applied for determining, prior to the use of the respirator, the threshold values of the most suitable respiratory parameters for optimum operation of the respirator. This analysis is also continuously conducted during the operation of the respirator, in order to adapt these thresholds to the breathing of the patients.

According to another embodiment, the system and the method according to the invention may be applied in tomodenistometry imaging (TMD), the analysis of the respiratory activity signals allowing correction, notably on the images of the lungs, of the artifacts due to respiratory movements.

However it should be understood that the exemplary embodiments presented above are not limiting.

Notably, the respiratory activity signal is not necessarily relative to the inhaled or exhaled air flow rate.

The invention claimed is:

1. A method of assisting the respiratory activity of a patient, comprising:
    placing a respiratory mask over the mouth and nose of the patient, wherein the respiratory mask comprises a pneumotachograph configured to measure flow rates of inhaled and exhaled air by the patient and to generate from the flow rates at least one respiratory activity signal comprising at least one elementary signal corresponding to a respiratory cycle, the general form of which may be expressed by $x(t)=x_0+x_1 \cos(\Phi(t))$, wherein t is time, $\Phi(t)$ is the phase of said elementary signal, $x_0$ and $x_1$ are coefficients;
    determining respiratory activity of the patient by performing an analysis of said respiratory activity signal, wherein the analysis of said respiratory activity signal comprises the following steps:
    extracting, from said respiratory activity signal, said elementary signal;
    determining an expression of a phase equation $$F(\Phi) = \frac{d\Phi}{dt}$$

of said elementary signal; and
determining an expression of the phase $\Phi(t)$ of said elementary signal as a function of parameters measuring an anharmonicity of said elementary signal and its morphology, from $p\cos_n$ and $p\sin_n$ functions defined by:

$$p\cos_n(t,r) = \sum_{k=1}^{\infty} \cos(kt)\frac{r^k}{k^n}$$

and $$p\sin_n(t,r) = \sum_{k=1}^{\infty} \sin(kt)\frac{r^k}{k^n}.$$

wherein r is an anharmonicity parameter measuring the degree of anharmonicity of the signal, the limit r=0 corresponding to a harmonic signal, the limit r=1 to an infinitely anharmonic signal, and k and n are integers; and
    controlling respiration of the patient based on the respiratory activity of the patient.

2. The method of assisting respiratory activity according to claim 1, wherein the phase equation is expressed as:

$$\frac{d\Phi}{dt} = \frac{1+r^2+2r\cos(\Phi)}{1-r^2},$$

wherein r, varying in [0,1], is a parameter measuring the anharmonicity of said elementary signal.

3. The method of assisting respiratory activity according to claim 2, wherein the elementary signal is expressed by two parameters r and $\Phi_0$, as:

$$x(t)=x_0+a_1 h\sin(t,r)+b_1 h\cos(t,r)$$

wherein $a_1=x_1\cos(\Phi_0)$, $b_1=-x_1\sin(\Phi_0)$, and $\Phi_0$ is a phase origin, the h sin and h cos functions being defined by:

$$h\cos: (t, r) \to \frac{(1+r^2)\cos(t) + 2r}{1 + r^2 - 2r\cos(t)}$$

and $$h\sin: (t, r) \to \frac{(1-r^2)\sin(t)}{1 + r^2 - 2r\cos(t)}.$$

4. The method of assisting respiratory activity according to claim 1, wherein the phase equation is expressed as:

$$F(\Phi) = \frac{P(\Phi)}{Q(\Phi)},$$

wherein $P(\Phi)$ and $Q(\Phi)$ are trigonometric polynomials.

5. The method of assisting respiratory activity according to claim 4, wherein the expression of the phase $\Phi(t)$ is determined as:

$$t(\Phi) = \Phi + \sum_{k=1}^{n} a_k p\sin_1(\Phi - p_k, r_k) - b_k p\cos_1(\Phi - p_k, r_k)$$

wherein the $p\sin_1$ and $p\cos_1$ functions are defined by:

$$p\cos_1(t, r) = \sum_{k=1}^{\infty} \cos(kt)\frac{r^k}{k}$$

and $$p\sin_1(t, r) = \sum_{k=1}^{\infty} \sin(kt)\frac{r^k}{k}.$$

\* \* \* \* \*